United States Patent [19]

Brånemark

[11] Patent Number: 5,564,926
[45] Date of Patent: Oct. 15, 1996

[54] ANCHORING ELEMENT FOR ANCHORAGE IN BONE TISSUE

[75] Inventor: Per-Ingvar Brånemark, Mölndal, Sweden

[73] Assignee: Medevelop AB, Gothenburg, Sweden

[21] Appl. No.: 326,216

[22] Filed: Oct. 20, 1994

Related U.S. Application Data

[63] Continuation-in-part of Ser. No. 154,183, Nov. 18, 1993, Pat. No. 5,362,236.

[30] Foreign Application Priority Data

Nov. 26, 1992 [SE] Sweden ................................ 92035623

[51] Int. Cl.⁶ ............................................. A61C 8/00
[52] U.S. Cl. ......................................... 433/174; 433/173
[58] Field of Search ................................ 433/172, 173, 433/174, 175, 176

[56] References Cited

U.S. PATENT DOCUMENTS

| | | | |
|---|---|---|---|
| 3,499,222 | 3/1970 | Linkow | 433/174 |
| 4,463,753 | 8/1984 | Gustilo | 606/73 |
| 4,762,492 | 8/1988 | Nagai | 433/174 |
| 4,934,935 | 6/1990 | Edwards | 433/174 |
| 5,180,382 | 1/1993 | Frigg et al. | 606/65 |
| 5,199,873 | 4/1993 | Schulte et al. | 433/174 |

FOREIGN PATENT DOCUMENTS

| | | |
|---|---|---|
| 0424734 | 2/1991 | European Pat. Off. . |
| 0438048 | 7/1991 | European Pat. Off. . |
| 0491211 | 6/1992 | European Pat. Off. . |
| 4036753 | 5/1992 | Germany ............ 433/174 |
| 0505898 | 12/1954 | Italy .................... 433/174 |
| 1697781 | 12/1991 | U.S.S.R. ............. 433/173 |
| 1718892 | 3/1992 | U.S.S.R. ............. 433/174 |
| 9118556 | 12/1991 | WIPO . |

*Primary Examiner*—Christopher A. Bennett
*Attorney, Agent, or Firm*—Ostrolenk, Faber, Gerb & Soffen, LLP

[57] ABSTRACT

An anchoring element for implantation into first and second aligned bores of different diameters provided in bone tissue of two bones or two portions of a bone separated by a non-ossified tissue. A prosthesis is supported on the proximal end of the anchoring element. A first cylindrical portion is located at the distal end of the anchoring element and has a first external thread and an outer diameter corresponding to a diameter of the first bore. A second cylindrical portion is located at the proximal end of the anchoring element. The second cylindrical portion includes a second external thread and has an outer diameter corresponding to a diameter of the second bore. The first and second external threads have an equal pitch.

22 Claims, 2 Drawing Sheets

ANCHORING ELEMENT FOR ANCHORAGE IN BONE TISSUE

RELATED APPLICATION

This is a continuation-in-part application of U.S. application Ser. No. 08/154,183, filed Nov. 18, 1993, now U.S. Pat. No. 5,362,236.

BACKGROUND OF THE INVENTION

1. Field of the Invention

The present invention relates to an anchoring element of a biocompatible material for implantation in the bone tissue of two bones or two portions of a bone separated by non-ossified tissue and, more particularly, to a doubly anchored dental fixture for replacement of one of several teeth in the upper jaw.

2. Description of the Related Art

Known anchoring elements or fixtures are of a generally cylindrical form and provided with outer threads. They are adapted to be screwed into holes drilled in the respective bone. In certain cases, particularly in cases where substantial bone resorption has occurred, the appropriate bone holding the anchoring element or fixture of a prosthesis may be too weak to bear the load of a prosthesis. In such case, the load might be reduced by multiple anchoring, for instance, by anchoring the fixture in two bones or two portions of the same bone.

An appropriate example of the above situation is a patient who has been edentulous for a long time. For this reason, the patient's jawbone has become partly resorbed and its retention capacity has become inadequate for the anchoring of one or several dental fixtures. Such a patient may not be successfully treated by implanting a desirable prosthetic appliance, or may not be willing to accept the substantial risk which accompanies dental surgery in such circumstances. The patient might lose the prosthesis or risk jawbone fracture.

U.S. Pat. No. 5,199,873 discloses a dental implant intended to be anchored completely in the jaw bone. The outside surface of the fixture is stepped downwardly by a plurality of steps, each of which is threaded. The implant is inserted in a corresponding stepped bore in the jawbone. Only the last stepped portion is screwed into the jawbone. Thus, the implant is not screwed into the jawbone over its entire length, of but only over a small length, significantly reducing trauma. However, the bore in the jaw must be provided with steps dimensioned similarly to the stepped portions of the implant, which requires a multi-step, difficult drilling process.

SUMMARY OF THE INVENTION

An object of the present invention is to provide an anchoring element of a biocompatible material, which is optimally designed for implantation in the bone tissue of two bones or two portions of a bone separated by non-ossified tissue, for distributing the load from a prosthesis attached to the anchoring element between the two bones or bone portions.

It is another object of the invention to provide a dental anchoring element of a biocompatible material, which is optimally designed for implantation in the maxilla and the zygomatic bone, for distributing the load caused by a dental prosthesis attached to the anchoring element.

These and other objects are achieved by providing a substantially rotationally symmetric anchoring element of a biocompatible material for implantation into aligned bores of different widths provided in the bone tissue of two bones or two portions of a bone separated by non-ossified tissue. The anchoring element has a distal insertion end and a proximal supporting end, and includes:

means for supporting a prosthesis, such as an artificial joint component, a tooth bridge, or an artificial tooth, located on the proximal supporting end of the anchoring element;

a first cylindrical portion, located at the distal insertion end of the anchoring element, provided with a first external thread and having an outer diameter corresponding to a diameter of the first bore;

a second cylindrical portion, located at the proximal supporting end of the anchoring element, provided with a second external thread and having a diameter corresponding to a diameter of the second bore; and an intermediate cylindrical portion disposed between the first and second cylindrical portions and having a length approximately equal to the width of the non-ossified tissue between the bones.

The outer diameter of the first cylindrical portion is equal to or smaller than the diameter of the second cylindrical portion. The first and second external threads have an equal pitch.

In one embodiment, the threads of the first and second threaded cylindrical portions extend completely across the full length of the intermediate cylindrical portion and merge to form an integral outer thread.

In another embodiment, at least a part of the intermediate cylindrical portion is free from threads. The thread-free part of the cylindrical intermediate portion and the threads of the first cylindrical portion preferably have substantially the same outer diameter.

It is preferred that the support means includes an inner threaded bore at the supporting end.

It is also preferred that the combined length of the first threaded cylindrical portion and the intermediate cylindrical portion is at least four times greater than the length of the second threaded cylindrical portion.

A particularly preferred embodiment according to the invention is a dental anchoring element of a biocompatible material, for implantation into first and second aligned bores of different diameters provided in the bone tissue of the maxilla and the zygomatic bone. The anchoring element has a distal insertion end and a proximal supporting end, and includes:

means for supporting a tooth prosthesis, such as one or several artificial teeth or a tooth bridge construction, located on the proximal end of the anchoring element.

a first cylindrical portion, located at the distal insertion end of the anchoring element, including a first external thread and having an outer diameter corresponding to the diameter of the first bore in the zygomatic bone;

a second cylindrical portion, located at the distal insertion end of the anchoring element, having a second external thread and an outer diameter corresponding to the diameter of the second bore provided in the maxilla;

an intermediate cylindrical portion disposed between the first and second cylindrical portions and having a length approximately equal to the width of a maxillary sinus disposed between the maxilla and the zygomatic bone.

The outer diameter of the first cylindrical portion is equal to or smaller than the diameter of the second cylindrical portion, and the first and second outer threads having the same pitch.

It is preferred that the support end of the anchoring fixture includes an inner threaded bore and at least one abutment area for abutment of the tooth prosthesis. The threaded bore is preferably positioned at an angle with respect to the rotational axis of the anchoring element, the angle being in the range of between 15° and 60°, preferably about 45°.

It is preferred that the dental fixture include, at its insertion end, an axial bore and through slits of substantially axial extension.

It is furthermore preferred that the anchoring fixture include, at its supporting end, a periosteal collar plate or foil of pure titanium or another biocompatible material provided with through pores having a preferred diameter of from about 0.1 mm to about 0.01 mm. Preferably, the periosteal collar plate or foil has a thickness of from about 0.1 to about 0.3 mm.

Other variations, modifications, and advantageous features of the invention will become apparent from the following description of the preferred, non-limiting embodiments of the dental anchoring element of the present invention with reference to the attached drawings.

DETAILED DESCRIPTION OF THE PREFERRED EMBODIMENTS

The anchoring element of the present invention is substantially symmetrically cylindrical and has a proximal supporting end, supplied with supporting means to receive, directly or indirectly after healing into the bone, a prosthesis, artificial joint component, tooth bridge, or artificial tooth, etc.

Such anchoring elements are known in the art—see, e.g., U.S. Pat. No. 5,064,425. The insertion end is supplied with an outer thread, whereby the anchoring element can be screwed into a drilled hole in the bone. The hole has a slightly smaller diameter than the outer diameter of the thread of the anchoring element. In this case, the thread should preferably be self-tapping, as exemplified in U.S. Pat. No. 5,064,425.

In order to achieve optimal healing and integration with surrounding bone tissue, the surface of the anchoring element should preferably be provided with micropits within the size range of 10–1000 nm, as described, for example, in U.S. Pat. No. 4,330,891.

Figure 1:
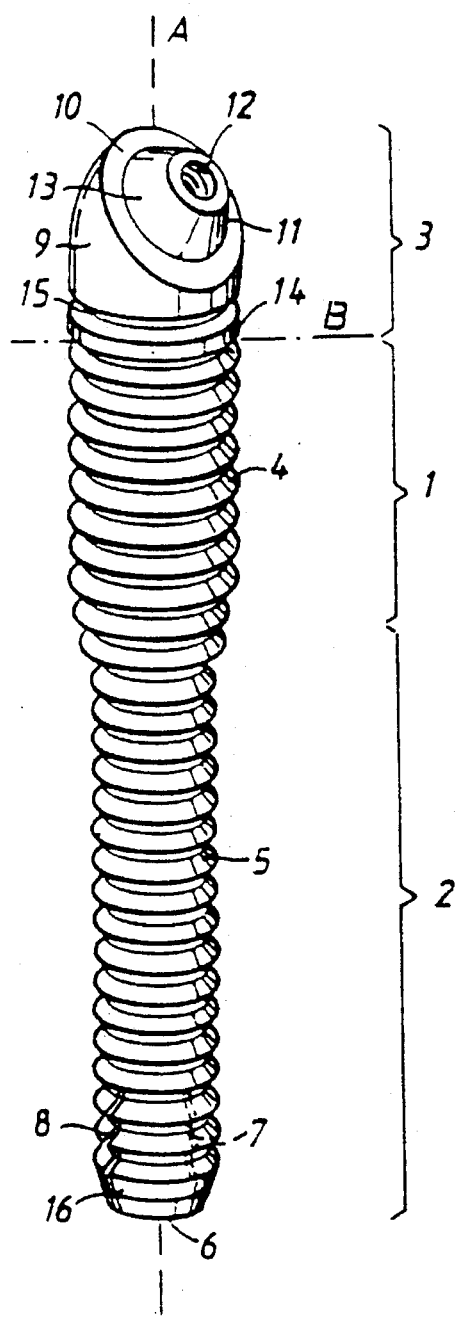
FIG. 1 is a slightly oblique side view of the anchoring element according to a first embodiment of the present invention.

The fixture shown in FIG. 1 is manufactured as a single piece of pure titanium and essentially composed of two cylindrical segments 1, 2 bordering each other and being in alignment. Cylindrical segment 1 is proximal to the jaw and has a diameter larger than that of cylindrical segment 2, which is distal to the jaw.

The outer surface of the fixture is threaded, except for a mounting section 3 extending from the proximal end of the fixture and connected to the cylindrical proximal segment 1. The outer threads comprise second thread 4 on the proximal cylindrical segment 1 and first thread 5 on the distal cylindrical segment 2. The pitch is the same for both threads 4, 5, which merge at the border zone between the cylindrical segments. The inner diameter of the first thread 4 is somewhat but not much larger than the outer diameter of the second thread 5. Threads 4, 5 are self-tapping.

A symmetrically centered bore (not shown) extends inward from the distal end 6 and has an extension corresponding to about half the length of the proximal segment 2. Two through slits 7, 8 arranged symmetrically in segment 2 and in its axial longitudinal direction extend from a plane perpendicular to the central axis near the distal end 6 for a length of about three thread pitches. Slits 7 and 8 establish communication between the outside of proximal segment 1 and the symmetrically centered bore arranged therein for transport of bone material removed by ablation. The outside of distal segment 2 is bevelled towards end 6 as indicated by reference numeral 16.

The mounting section 3 includes a cylindrical chamber with a diameter corresponding to the outer diameter of segment 1. The mounting section 3 includes a base portion 9 having the form of a cylindrical body bisected by a plane at an angle of 45° with respect to the rotational axis of the element. The circular base of base 9 is connected to the proximal end of cylindrical segment 1 with which it merges. Nearest to the proximal segment, base portion 9 has an annular flange 14 to which an annular groove 15 connects in the direction of the proximal end. End face 10 of base portion 9 is defined by the aforementioned bisected plane and, at its proximal zone, smoothly rounded to join the cylinder mantle of base portion 9, the beading decreasing gradually towards the distal end of the base portion. Because of the bevelling, the profile of end face 10 is substantially circular.

In its center end, face 10 has a bore 12 extending at an angle of 45° with respect to longitudinal axis A for cylindrical segments 1 and 2, i.e., for the fixture. At bore 12, base portion 9 is extended by the formation of a frustum cone 11 tapering in a direction away from base portion 9. Mantle surface 13 of the frustum cone 11 and the annular end face 10 are designed for sealing abutment of a dental prosthesis or bridge (not shown) that can be mounted on the base portion by screw means.

Figure 2:
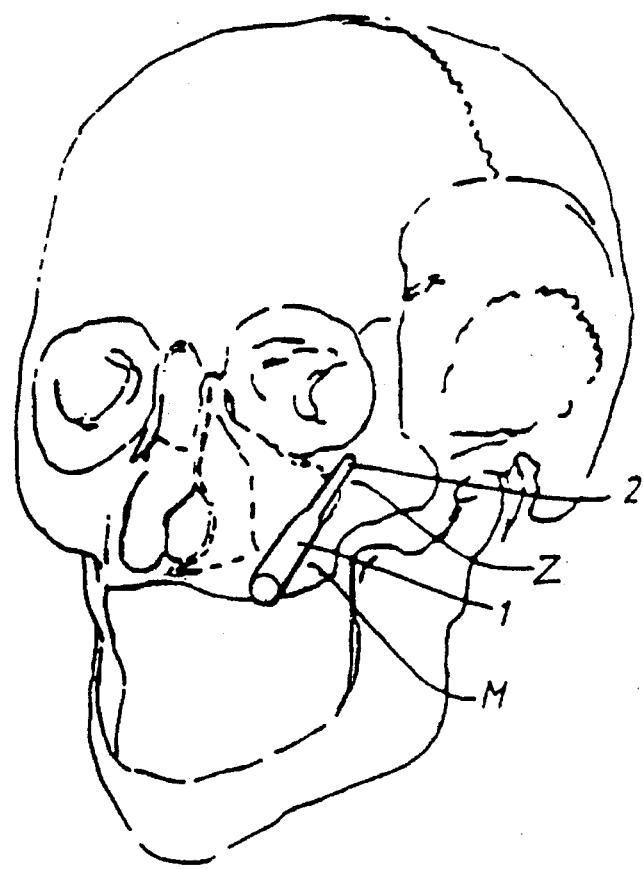
FIG. 2 is a schematic view illustrating the orientation of the anchoring element of FIG. 1 in situ after implantation in the maxilla and the zygomatic bone.

Implantation starts by providing, in the maxilla, a bore with a diameter corresponding to the diameter of threads 4 and at an angle deviating about 45° from the vertical (the longitudinal axis of the human body in an upright position), followed by a bore in the zygomatic bone having a diameter corresponding to the diameter of threads 5 and in line with the first hole. Thereupon, the fixture is inserted with its narrow end 6 entering into the hole in the upper jaw until, by means of its bevelled portion, it comes engaged with the hole arranged in the zygomatic bone. Thereupon, the fixture is screwed into the hole in the zygomatic bone in a self-tapping manner and, after threads 4 have reached the jaw bone, also simultaneously into the latter in a self-tapping manner. When attaining a sufficient insertion depth for the fixture, such depth being defined by the fixture's free end having the correct distance from the jaw bone, the screwing process is stopped. By fine tuning, that is, counter-clockwise or clockwise rotation around its longitudinal axis, bore 12 provided with internal threads is brought into correct position for mounting of the prosthesis, i.e., in a position in which bore 12 is substantially parallel with the longitudinal axis of the human body. The position for an implanted fixture according to the invention is schematically shown in FIG. 2. The zygomatic bone has been designated by 2 and the maxilla by M.

The dental prosthesis or bridge can be mounted after surgery or after a healing period during which the fixture is progressively anchored in bone tissue.

The length of the fixture and cylindrical segments 1 and 2 and the angle of bore 12 in base portion 9 are adapted to the anatomical requirements of the individual patient. A limited range of fixtures according to the invention, including fixtures of varied total length, varied ratio of length of the cylindrical segments, and varied angle of bore 12 in base portion 9 in relation to the longitudinal axis of the fixture, will suffice for covering the needs of most patients.

It is also possible to manufacture the fixture in two parts, a separate base portion 9 and segments 1, 2 provided with external threads. The base portion and the segments with external threads can be connected in various ways, for instance, by a symmetrically centered tap positioned on the end of base portion 9 facing away from bore 12, the tap being arranged for screwing into a threaded bore in the free end of segment 1 provided with external threads, both parts otherwise having planar abutting surfaces (line B in FIG. 1 indicates their position) for abutment against each other.

Figure 3:
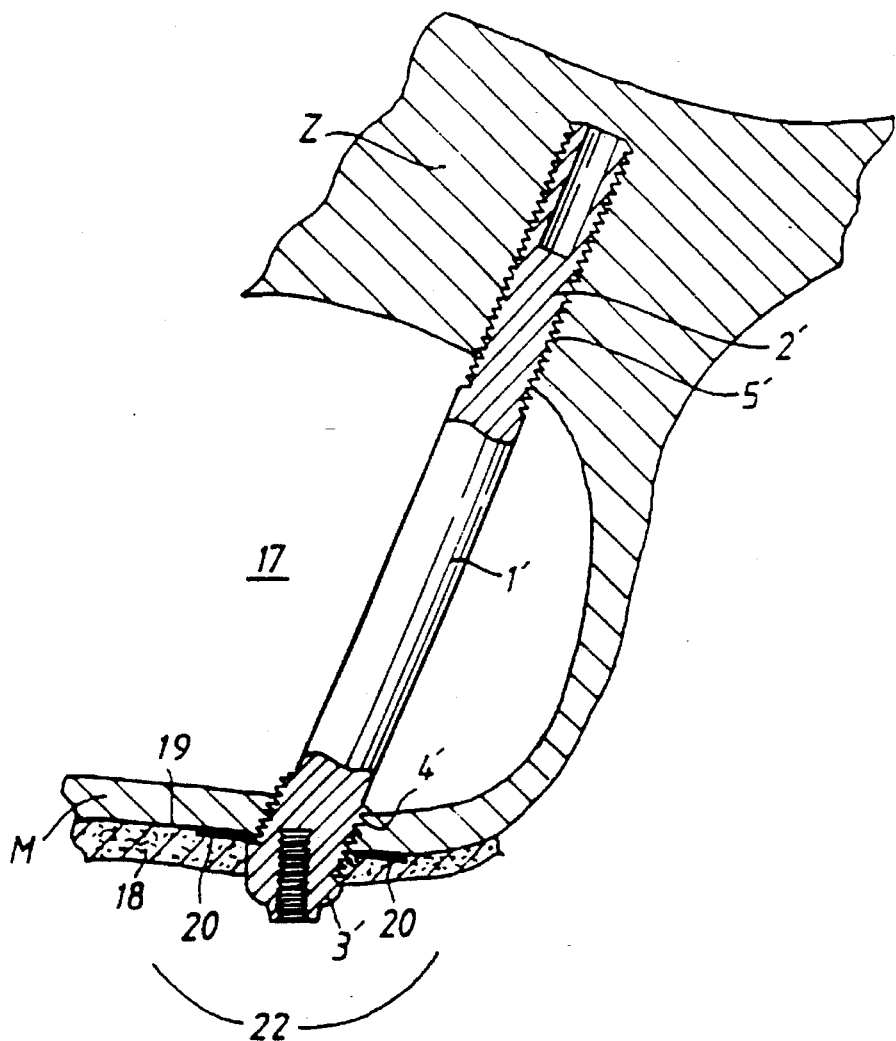
FIG. 3 is a cross-sectional view of an anchoring element according to a second embodiment of the present invention provided with a periosteal plate, in situ after implantation in the maxilla and the zygomatic bone and in section.

In the second embodiment of the fixture of the invention, shown in FIG. 3, only a proximal section of the proximal segment 1' includes second external thread 4'. The rest of the proximal segment 1' has a polished surface, i.e., essentially the portion positioned upon implantation in the maxillary sinus 17 between the maxilla M and the zygomatic bone Z. Second external thread 4' thus has an extension essentially corresponding to the depth of the through bore provided in the maxilla M in preparation for implantation. The distal segment 2' is provided with corresponding first external thread 5'.

Figure 4:
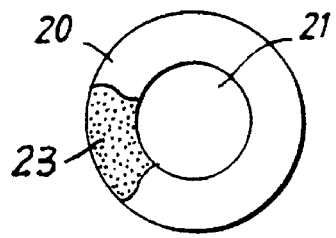
FIG. 4 is a top view of the periosteal plate of FIG. 3.

As is also shown in FIG. 3, this second embodiment can be provided (as can the first embodiment shown in FIG. 1) with a periosteal plate or foil 20 for enhancement of integration of the implant with living tissue in an area where the distal end zone of distal segment 2' with mounting section 3' emerges from the through bore in the maxilla M. The periosteal plate or foil 20 is a porous disc of thin pure titanium, preferably from about 0.1 to about 0.3 mm thick and having a concentric hole 21, as shown in FIG. 4, with a diameter slightly larger than the largest outer diameter of the fixture 1', 2', 3', allowing plate or foil 20 to be fitted like a collar around the part of the fixture protruding from the maxilla M. Periosteal plate or foil 20 is fitted with its one side against outer surface 19 of the maxilla M after partial removal of the periosteum 18 (the thickness of periosteum 18 is exaggerated in FIG. 3 for reasons of comprehensiveness) which is then folded back against the other side of the periosteal plate or foil 20. The pores 23 in the periosteal foil or plate 20 are through pores and provide for communication between both sides of foil or plate 20. It is preferred that the pores to have an average diameter of from about 0.01 to about 0.1 mm. The periosteal foil or plate 20 promotes anchoring of the fixture around its proximal part and reduces the risk of communication between the oral cavity 22 and the maxillary sinus 17.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. An anchoring element for implantation into first and second aligned bores of different diameters provided in bone tissue of two bones or two portions of a bone separated by non-ossified tissue, the anchoring element comprising:

a distal insertion end having a first cylindrical portion including a first external thread and having an outer diameter for corresponding to a diameter of the first bore;

a proximal supporting end having means disposed thereon for supporting a prosthesis and having a second cylindrical portion disposed on the proximal supporting end, the second cylindrical portion including a second external thread and having an outer diameter for corresponding to a diameter of the second bore; and an intermediate cylindrical portion disposed between the first and second cylindrical portions and having a length for approximately equalling a width of the non-ossified tissue between the bones and being free from threads;

wherein the outer diameter of the first cylindrical portion is equal to or smaller than the outer diameter of the second cylindrical portion, and wherein the first and second external threads have an equal pitch.

2. The anchoring element of claim 1, wherein the first and second external threads extend completely across the intermediate cylindrical portion and merge to form an integral external thread.

3. The anchoring element of claim 1, wherein the supporting means includes a threaded bore.

4. The anchoring element of claim 1, wherein the thread-free part of the intermediate cylindrical portion and the threads of the first cylindrical portion have substantially equal outer diameters.

5. The anchoring element of claim 1, wherein the external threads of the first and second cylindrical portions have an axial distance between two adjacent threadturns, and the intermediate cylindrical portion free from threads has an axial extension greater than the axial distance.

6. The anchoring element of claim 1, wherein the intermediate cylindrical portion free from threads has an axial extension greater than the outer diameter of the first cylindrical portion.

7. A dental anchoring element of a biocompatible material for implantation into first and second aligned bores of different diameters provided in a zygomatic bone and in a maxilla, the anchoring element having comprising:

a distal insertion end having a first cylindrical portion at the distal insertion end, the first cylindrical portion including a first external thread and having an outer diameter for corresponding to a diameter of the first bore in the zygomatic bone;

a proximal supporting end having means disposed thereon for supporting a tooth prosthesis and having a second cylindrical portion at the proximal supporting end, the second cylindrical portion including a second external thread and having an outer diameter for corresponding to a diameter of the second bore in the maxilla; and an intermediate cylindrical portion disposed between the first and second cylindrical portions and having a length for approximately equalling a width of a maxillary sinus disposed between the maxilla and the zygomatic bone;

wherein the outer diameter of the first cylindrical portion is at least equal to or smaller than the outer diameter of the second cylindrical portion, and the first and second external threads have an equal pitch.

8. The anchoring element of claim 7, wherein the first and second external threads extend completely across the intermediate cylindrical portion and merge to form an integral external thread.

9. The anchoring element of claim 7, wherein the supporting means includes a threaded bore and at least one abutment area, the anchoring element further comprising the tooth prosthesis, the tooth prosthesis abutting against the abutment area when installed.

10. The anchoring element of claim 9, wherein the threaded bore is positioned at an angle between 15° to 60° with respect to a rotational axis of the anchoring element.

11. The anchoring element of claim 10, wherein the bore is positioned an angle of 45° with respect to the rotational axis of the anchoring element.

12. The anchoring element of claim 7, wherein the insertion end includes an axial bore and a plurality of axially extending through slits.

13. The anchoring element of claim 7, wherein the thread-free intermediate portion and the first threaded cylindrical portion have substantially equal outer diameters.

14. The anchoring element of claim 7, further comprising means located at the proximal supporting end for promoting anchoring of the element in the maxilla.

15. The anchoring element of claim 14, wherein the anchoring means comprises a periosteal collar plate.

16. The anchoring element of claim 14, wherein the anchoring means comprises a foil.

17. The anchoring element of claim 14, wherein the anchoring means is made of a biocompatible material.

18. The anchoring element of claim 14, wherein the anchoring means is made of pure titanium.

19. The anchoring element of claim 14, wherein the anchoring means includes a plurality of through pores. Each of the plurality of through holes having a diameter in the range of 0.001 to 0.1 mm.

20. The anchoring element of claim 14, wherein the anchoring means has a thickness in the range of 0.1 to 0.3 mm.

21. The anchoring element of claim 7, wherein the external threads of the first and second cylindrical portions have an axial distance between two adjacent threadturns, and the intermediate cylindrical portion free from threads has an axial extension greater than the axial distance.

22. The anchoring element of claim 7, wherein the intermediate cylindrical portion free from threads has an axial extension greater than the outer diameter of the first cylindrical portion.

* * * * *